United States Patent
Furudono

(10) Patent No.: US 11,266,181 B2
(45) Date of Patent: Mar. 8, 2022

(54) HEATING-TYPE FLAVOR INHALER

(71) Applicant: JAPAN TOBACCO INC., Tokyo (JP)

(72) Inventor: Yuichi Furudono, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 454 days.

(21) Appl. No.: 16/252,125

(22) Filed: Jan. 18, 2019

(65) Prior Publication Data

US 2019/0150512 A1   May 23, 2019

Related U.S. Application Data

(63) Continuation of application No. PCT/JP2016/071277, filed on Jul. 20, 2016.

(51) Int. Cl.
| | |
|---|---|
| *A24F 40/42* | (2020.01) |
| *A24F 40/40* | (2020.01) |
| *A61M 15/06* | (2006.01) |
| *A24F 40/10* | (2020.01) |
| *A24F 40/20* | (2020.01) |
| *A61M 11/04* | (2006.01) |
| *A24B 15/167* | (2020.01) |

(52) U.S. Cl.
CPC .............. *A24F 40/40* (2020.01); *A24F 40/42* (2020.01); *A61M 15/06* (2013.01); *A24B 15/167* (2016.11); *A24F 40/10* (2020.01); *A24F 40/20* (2020.01); *A61M 11/042* (2014.02)

(58) Field of Classification Search
CPC ................................. A24F 40/40; A61M 15/06
USPC ........................................................ D27/100
See application file for complete search history.

(56) References Cited

U.S. PATENT DOCUMENTS

| | | | |
|---|---|---|---|
| 2010/0059070 A1 | 3/2010 | Potter et al. | |
| 2014/0041655 A1* | 2/2014 | Barron | A24F 40/46 |
| | | | 128/202.21 |
| 2014/0246032 A1 | 9/2014 | Scatterday | |
| 2014/0366899 A1 | 12/2014 | Plojoux et al. | |

(Continued)

FOREIGN PATENT DOCUMENTS

| | | |
|---|---|---|
| CN | 103783674 A | 5/2014 |
| CN | 103829381 A | 6/2014 |

(Continued)

OTHER PUBLICATIONS

CVvapor.com, Innokin iTaste Exthermal RDA Atomizer, Dec. 12, 2015 (downloaded online Apr. 21, 2021 from archive.org) (Year: 2015).*

(Continued)

*Primary Examiner* — Anthony Calandra
(74) *Attorney, Agent, or Firm* — Birch, Stewart, Kolasch & Birch, LLP

(57) ABSTRACT

Provided is a heating-type flavor inhaler in which heat generated when a flavor-generating source is electrically heated with a heater is not easily retained inside a casing. The heating-type flavor inhaler is provided with: a casing having an intake opening and the overall shape forming a tube; a flavor-generating source provided inside the casing; and a heater for electrically heating the flavor-generating source, the heater being provided inside the casing. A metal concavo-convex pattern for promoting heat dissipation is provided on the external peripheral surface of the casing in a position in which at least the heater is disposed.

8 Claims, 8 Drawing Sheets

(56) References Cited

U.S. PATENT DOCUMENTS

| | | | |
|---|---|---|---|
| 2014/0366900 | A1 | 12/2014 | Plojoux et al. |
| 2015/0020832 | A1 | 1/2015 | Greim et al. |
| 2016/0262449 | A1 | 9/2016 | Liu |
| 2016/0286864 | A1 | 10/2016 | Lin |

FOREIGN PATENT DOCUMENTS

| | | | |
|---|---|---|---|
| CN | 203828066 U | | 9/2014 |
| CN | 105361249 A | | 3/2016 |
| CN | 205337595 U | | 6/2016 |
| JP | 47-42455 Y1 | | 12/1972 |
| JP | 60-64194 A | | 4/1985 |
| JP | 2-102995 U | | 8/1990 |
| JP | 2010-520742 A | | 6/2010 |
| JP | 2015-504668 A | | 2/2015 |
| KR | 10-2008-0060216 A | | 7/2008 |
| KR | 10-1329162 B1 | | 11/2013 |
| WO | WO 2007/012007 A2 | | 1/2007 |

OTHER PUBLICATIONS

Mehmet Kanoglu, Heat Transfer from Finned Surfaces (withexcerts from Fundamentals of Thermal-Fluid Scienced by Cenegel et al., 2008), 2014 [downloaded online Apr. 23, 2021 from google.com]. (Year: 2014).*

Saeed Almalowi, Heat Transfer—ME 372, 2015. (Year: 2015).*

Japanese Office Action for Japanese Application No. 2018-528146, dated Sep. 10, 2019, with an English translation.

European Search Report issued in European Patent Application No. 16909505.6 dated Feb. 26, 2020.

Korean Office Action for Korean Application No. 10-2019-7004092, dated Aug. 24, 2020, with English translation.

Chinese Office Action and Search Report dated Sep. 24, 2020 for Application No. 201680087803.2 along with an English translation of the Office Action.

International Search Report (Form PCT/ISA/210), dated Sep. 13, 2016, for International Application No. PCT/JP2016/071277.

International Search Report (For PCT/ISA/210), dated Jan. 31, 2019, for International Application No. PCT/JP2016/071277.

International Preliminary Report on Patentability and an English Translation of the Written Opinion of the International Searching Authority, dated Jan. 31, 2019, for International Application No. PCT/JP2016/071277.

Taiwanese Office Action and Search Report, dated Apr. 25, 2017, for Taiwanese Application No. 105123041, with an English translation.

* cited by examiner

HEATING-TYPE FLAVOR INHALER

CROSS-REFERENCE TO RELATED APPLICATIONS

This application is a continuation application of International Application PCT/JP2016/071277 filed on Jul. 20, 2016 and designated the U.S., the entire contents of which are incorporated herein by reference.

TECHNICAL FIELD

The present invention relates to a heating-type flavor inhaler.

BACKGROUND ART

Smoking articles such as cigarettes and cigars are typical flavor inhalers that produce smoke (aerosol) containing a flavor component of tobacco by burning tobacco leaves. In recent years, there have been proposed various flavor inhalers that allow inhaling of flavor by heating a flavor generating source with heat, which is generated from an electric heater having an electric heating coil or the like, without burning or thermally decomposing the flavor generating source.

As a heating-type flavor inhaler of this kind, there is a known electronic cigarette including: a cylindrical casing that has a mouthpiece opening and guides a produced airflow toward the mouthpiece opening; a flavor generating source arranged in the casing; and a heater for electrically heating the flavor generating source.
[Patent document 1] U.S. Patent Application No. 2014/0246032
[Patent document 2] Chinese Utility Model No. 203828066

SUMMARY OF THE INVENTION

Technical Problem

However, in the above heating-type flavor inhaler, the heat that is generated when the flavor generating source is heated by the heater tends to stay in the casing, and there is a concern that the influence of the heat accumulated in the casing may adversely affect the parts, the flavor generating source and the like in the flavor inhaler. The present invention has been made in view of the above circumstance, and it is an object of the present invention to provide a heating-type flavor inhaler in which heat that is generated when the flavor generating source is electrically heated by the heater is less likely to stay in the casing.

Solution to Problem

In the present invention to solve the above problems, on the casing of the heating-type flavor inhaler, a bumpy pattern that is made of metal and facilitates heat dissipation is provided on an outer circumferential surface of at least a position where a heater is arranged.

More specifically, a heating-type flavor inhaler according to the present invention includes: a casing having a mouthpiece opening and being cylindrical in overall shape; a flavor generating source provided in the casing; and a heater, provided in the casing, for electrically heating the flavor generating source, wherein a bumpy pattern that is made of metal and facilitates heat dissipation is provided on an outer circumferential surface of at least a position of the casing at which the heater is arranged. In the present invention, the bumpy pattern may be formed by arranging a pattern of protrusions on the outer circumferential surface of the casing, or by arranging a pattern of dent portions on the outer circumferential surface of the casing by, for example, cutting and the like.

Moreover, in the heating-type flavor inhaler according to the present invention, the heater may be arranged in a central region in a longitudinal direction of the casing, in a bumpy-pattern-arranged section where the bumpy pattern is formed.

Here, the bumpy pattern may include a plurality of protrusions aligned on the outer circumferential surface of the casing.

Further, in the heating-type flavor inhaler according to the present invention, a no-bumpy-pattern-arranged section where the bumpy pattern is not provided may be formed over a predetermined section from a mouthpiece-opening end of the casing in a longitudinal direction.

Here, in the heating-type flavor inhaler according to the present invention, a height dimension of each of the protrusions in the bumpy pattern may be larger than a width dimension of the protrusion.

Furthermore, in the heating-type flavor inhaler according to the present invention, each of the protrusions in the bumpy pattern may have a tapered shape toward a top portion.

Additionally, in the heating-type flavor inhaler according to the present invention, a heat insulating material may be provided on a top portion of each of the protrusions in the bumpy pattern.

Effects of the Invention

According to the present invention, it is possible to provide the heating-type flavor inhaler in which heat that is generated when the flavor generating source is electrically heated by the heater is less likely to stay in the casing.

DESCRIPTION OF EMBODIMENT

Here, an embodiment of a heating-type flavor inhaler according to the present invention will be described based on the drawings. The dimensions, materials, shapes, relative arrangements, etc. of the component parts described in the present embodiment are not intended to limit the technical scope of the invention only to them, unless otherwise specified particularly.

Embodiment 1

Figure 1:
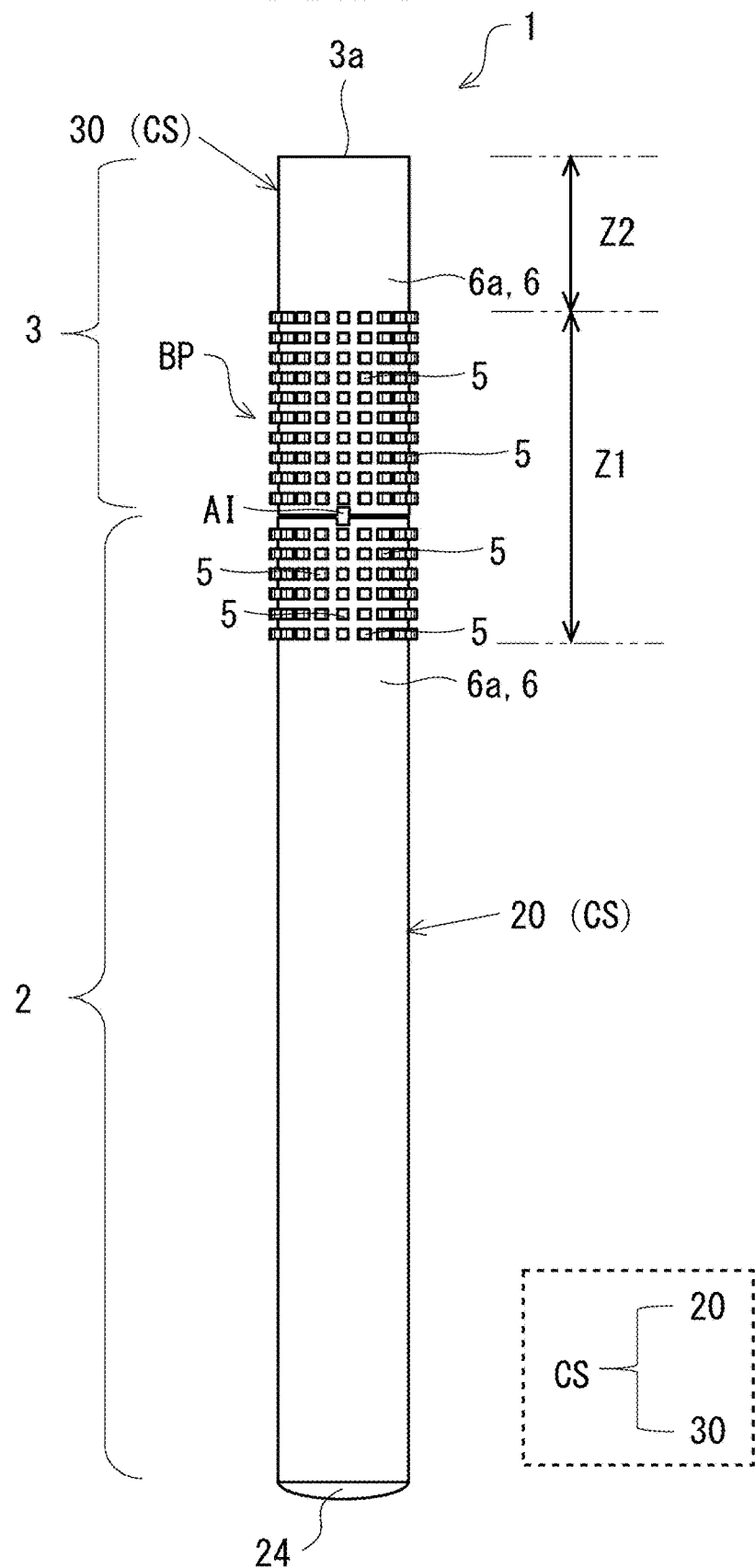
FIG. 1 is an external view of an electronic cigarette according to Embodiment 1.
Figure 2:
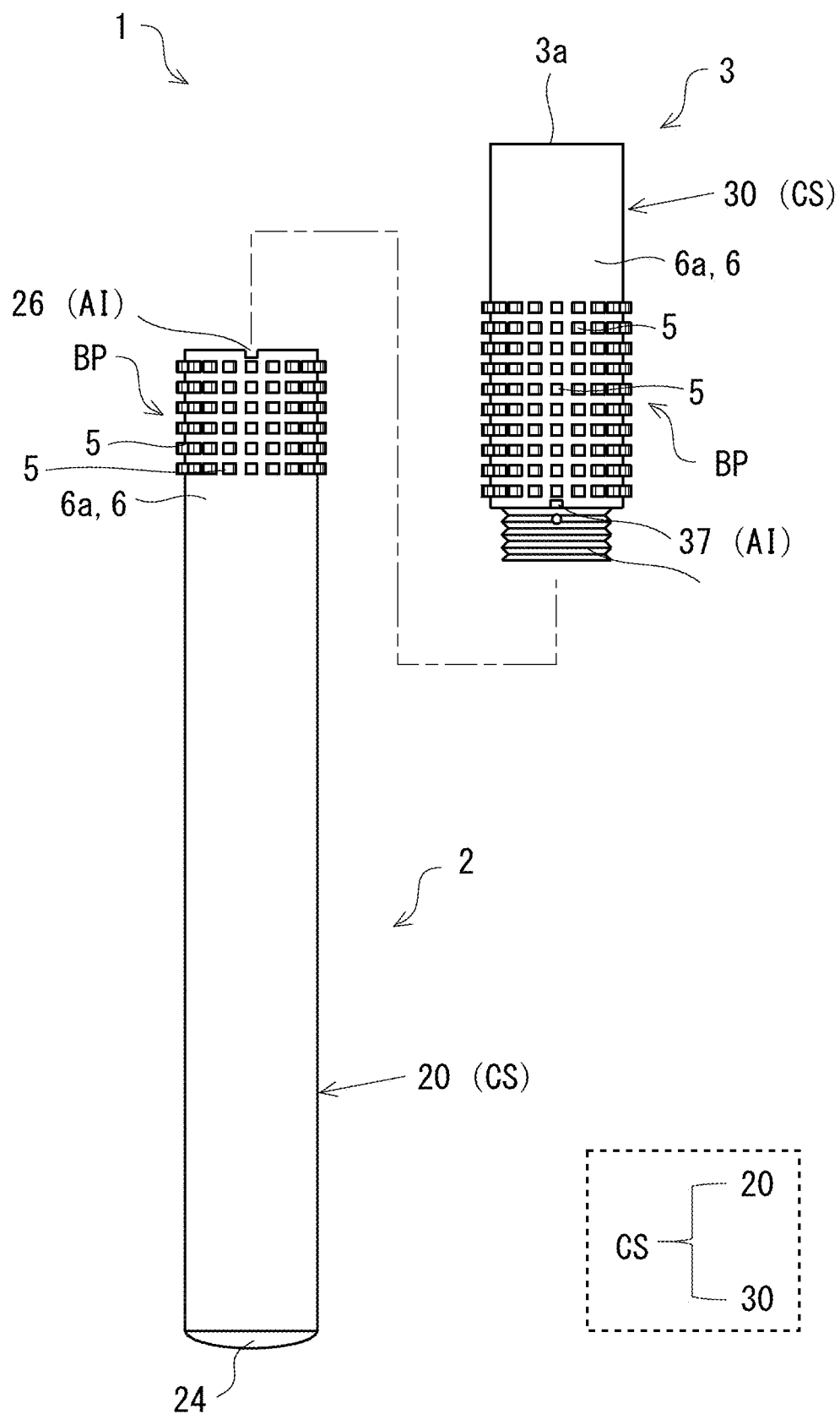
FIG. 2 is an external view of the electronic cigarette according to Embodiment 1.
Figure 3:
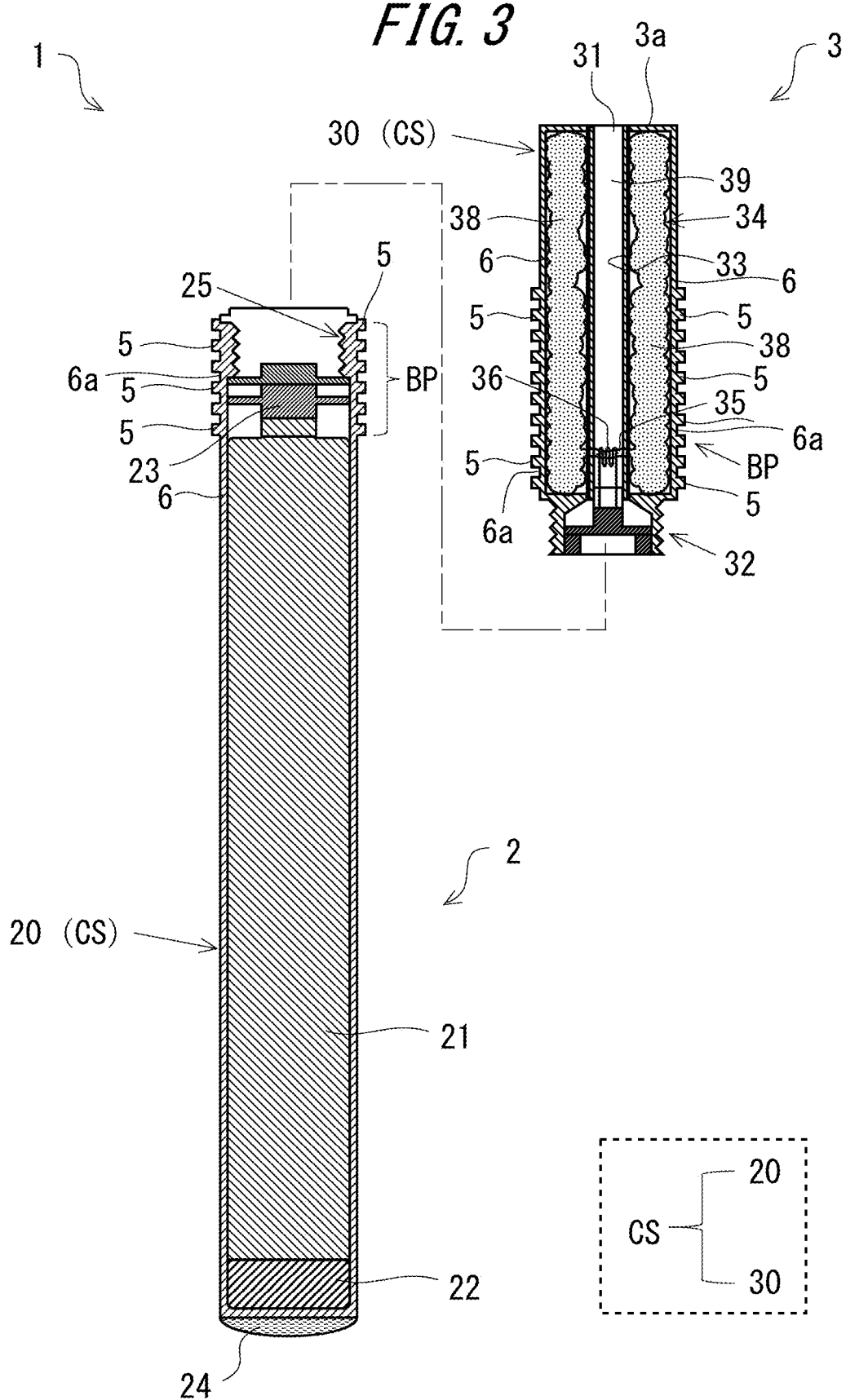
FIG. 3 is an internal structural view of the electronic cigarette according to Embodiment 1.

FIGS. 1 to 3 are schematic views of an electronic cigarette 1 as an example of a heating-type flavor inhaler according to Embodiment 1. FIGS. 1 and 2 are external views of the electronic cigarette 1 according to Embodiment 1. FIG. 3 is an internal structural view of the electronic cigarette 1 according to Embodiment 1.

In the electronic cigarette 1, a main body part 2 and a cartomizer part 3 are freely attachable to and detachable from each other. FIG. 1 illustrates a state in which the main body part 2 and the cartomizer part 3 are united. FIG. 2 illustrates a state in which the main body part 2 and the cartomizer part 3 are separated. Here, reference numeral 20 is a casing of the main body part 2 (hereinafter referred to as the "first casing"), and reference numeral 30 is a casing of the cartomizer part 3 (hereinafter referred to as the "second casing"). Hereinafter, when referring to the first casing 20 and the second casing 30 collectively, the first casing 20 and the second casing 30 are simply referred to as the "casing CS". The overall shape of the casing of the electronic cigarette 1 is a cylindrical shape (rod-like shape). In the present description, the term "casing" means a case that houses various parts of the electronic cigarette 1 and may be referred to as, for example, the "shell", "housing", or the like.

A battery 21, an electronic control unit 22, a suction detection sensor 23, etc. are housed in the first casing 20 of the main body part 2. Moreover, an LED 24 is provided on one end of the main body part 2. The battery 21 may be a rechargeable battery such as, for example, a lithium ion secondary battery. The electronic control unit 22 is a computer that controls the entire electronic cigarette 1. The electronic control unit 22 may be, for example, a microprocessor having a circuit board (not illustrated) on which a processor, a memory, etc. are mounted.

The first casing 20 is, for example, a cylindrical shell with a bottom, and the LED 24, the electronic control unit 22, the battery 21 and the suction detection sensor 23 are arranged from the bottom surface 20a side. Provided on the upper-end side of the first casing 20 is a first engagement part 25 that makes it possible to freely attach or detach the main body part 2 to or from the cartomizer part 3. Further, on the upper end of the first casing 20, a first air inlet hole 26, which is a cutout for taking outside air into the inside, is provided.

Next, the cartomizer part 3 will be described. The cartomizer part 3 is an assembly in which a heater unit and a cartridge section are united. The second casing 30 of the cartomizer part 3 is, for example, a cylindrical shell with a bottom, and a mouthpiece opening 31, which is a suction opening, is made at the center of an upper end surface 30a. The cartomizer part 3 also functions as a mouthpiece, and a user can inhale an aerosol generated in the cartomizer part 3 from the mouthpiece opening 31 by holding the upper-end side of the second casing 30 in his or her mouth and sucking. The mouthpiece-opening end side of the cartomizer part 3 may have a tapered shape toward the upper-end side to allow the user to easily hold the cartomizer part 3 in his or her mouth.

The lower-end side of the second casing 30 of the cartomizer part 3 is provided with a second engagement part 32 that makes it possible to freely attach or detach the cartomizer part 3 to or from the main body part 2. The second engagement part 32 of the cartomizer part 3 can be engaged with and disengaged from the first engagement part 25 of the main body part 2. Means for engaging the first engagement part 25 of the main body part 2 and the second engagement part 32 of the cartomizer part 3 is not particularly limited, and a screw connection method is adopted in the present embodiment. However, instead of the screw connection method, it is possible to use known connection means such as connection through a sleeve member, for example, fitting connection and the like. Furthermore, as illustrated in FIG. 2, a second air inlet hole 37, which is a cutout for taking outside air into the inside, is provided in the lower end portion of the second casing 30. In a state in which the cartomizer part 3 is attached to the main body part 2, the second air inlet hole 37 communicates with the first air inlet hole 26 of the main body part 2, and an air inlet AI is formed by a combination of the air inlet holes 37 and 26.

Next, the internal structure of the cartomizer part 3 will be described in detail. The inside of the second casing 30 of the cartomizer part 3 has a double cylinder structure, and the inner space of the second casing 30 is divided into a cartridge section 34 for storing an aerosol-generating liquid, and an internal passage 39 by a cylindrical partition wall 33. In the cartridge section 34, a liquid supply member 38, such as cotton fiber impregnated with the aerosol-generating liquid, is arranged. The aerosol-generating liquid is a liquid that generates an aerosol by being heated, and a polyol containing a flavoring is adopted in the present embodiment, although the aerosol-generating liquid is not particularly limited. For example, the aerosol-generating liquid may be a mixed solution of glycerin, propylene glycol, nicotine solution, water, flavoring, etc.

Reference numeral 35 is a wick that directly or indirectly sucks up and holds the aerosol-generating liquid stored in the cartridge section 34. The wick 35 may be, for example, a twisted glass fiber yarn. The wick 35 has a capillary structure, and can directly sucks up the aerosol-generating liquid stored in the cartridge section 34, or indirectly suck up the aerosol-generating liquid through the liquid supply member 38 made of cotton fiber impregnated with the aerosol-generating liquid liquid by utilizing a capillary phenomenon, and hold the aerosol-generating. The wick 35 is held by the partition wall 33 in a state of being inserted through a pair of holding holes (not illustrated) provided in the partition wall 33. As illustrated in FIG. 3, the wick 35 is placed across a transverse section of the internal passage 39, and is arranged in such a manner that both ends of the wick 35 extend to the inside of the cartridge section 34 and in contact with the liquid supply member 38 made of cotton fiber.

Moreover, as illustrated in FIG. 3, an electric heater 36 having an electric heating coil is wound around the wick 35. The wick 35 also functions as a core member that supports the electric heating coil of the electric heater 36. The electric heater 36 surrounds at least partially the center portion of the wick 35 in the longitudinal direction, and when the electric heater 36 is activated by conducting electricity, the wick 35 is heated and consequently the aerosol-generating liquid held in the wick 35 evaporates.

Here, the electronic control unit 22 and the battery 21 are connected through electric wiring, and conducting electricity from the battery 21 to the electric heater 36 is controlled by the electronic control unit 22. Here, the electronic cigarette 1 can detect a vaping request from the user by detecting sucking (puff) of the mouthpiece opening (suction opening)

31 by the user with the suction detection sensor 23 arranged in the main body part 2. For example, when the user sucks the mouthpiece opening 31, outside air is taken into the inside of the casing CS from the air inlet AI. Based on a pressure change inside the casing CS at this time, the suction detection sensor 23 can detect the sucking of the mouthpiece opening 31 by the user. When the suction detection sensor 23 detects the sucking of the mouthpiece opening 31 by the user, the electronic control unit 22 supplies power from the battery 21 to the electric heater 36 and heats the wick 35, thereby evaporating the aerosol-generating liquid.

As the suction detection sensor 23, it may be possible to use a pressure sensitive sensor or a thermal-type flow meter (MEMS flow sensor or the like) that detects a negative pressure produced due to the sucking by the user. Instead of the suction detection sensor 23, a vaping switch (not illustrated) for accepting a manipulation from the user may be provided in the casing CS of the electronic cigarette 1. In this case, the vaping switch is connected to the electronic control unit 22 through electric wiring, and the electronic control unit 22 detects turning on of the vaping switch. When the vaping switch is on, the electronic control unit 22 can evaporate the aerosol-generating liquid by conducting electricity to the electric heater 36 from the battery 21.

As illustrated in FIG. 2, the second air inlet hole 37, which is a cutout for taking outside air into the inside, is provided in the lower end portion of the second casing 30. In a state in which the cartomizer part 3 is attached to the main body part 2, the second air inlet hole 37 communicates with the first air inlet hole 26 of the main body part 2, and the air inlet AI is formed by a combination of these air inlet holes.

As described above, when the sucking of the mouthpiece opening 31 by the user is detected, the electronic cigarette 1 heats the wick 35 by conducting electricity to the electric heater 36, and evaporates (vaporizes) the aerosol-generating liquid held in the wick 35. In addition, the air flowing into the casing from the air inlet AI when the user sucks the mouthpiece opening 31 is guided to an inner end of the internal passage 39 in the cartomizer part 3. The mouthpiece opening 31 is provided at an outer end of the internal passage 39, and the air flowing into the internal passage 39 flows through the internal passage 39 toward the mouthpiece opening 31. Here, as illustrated in FIG. 3, in the course of the internal passage 39, the wick 35 that holds the electric heater 36 is placed across the internal passage 39. When the user sucks the mouthpiece opening 31, the aerosol-generating liquid which is evaporated (vaporized) by heating the wick 35 with the electric heater 36 is mixed with the air flowing in the internal passage 39, thereby generating an aerosol. Thus, the aerosol generated in the internal passage 39 is guided to the mouthpiece opening 31 through the internal passage 39, and the user can inhale the aerosol from the mouthpiece opening 31.

In the electronic cigarette 1 configured as described above, since the aerosol-generating liquid, which is a flavor generating source held in the wick 35, is heated with the electric heater 36, a large amount of heat may be generated by the electric heater 36. Here, if a large amount of heat is kept inside the casing CS, there is a concern that the respective components housed in the casing CS, for example, the electronic control unit 22 and the aerosol-generating liquid stored in the cartridge section 34 may be affected. Therefore, the casing CS of the electronic cigarette 1 according to the present embodiment employs a structure that facilitates release of heat generated by the electric heater 36 to the outside.

Figure 4A:
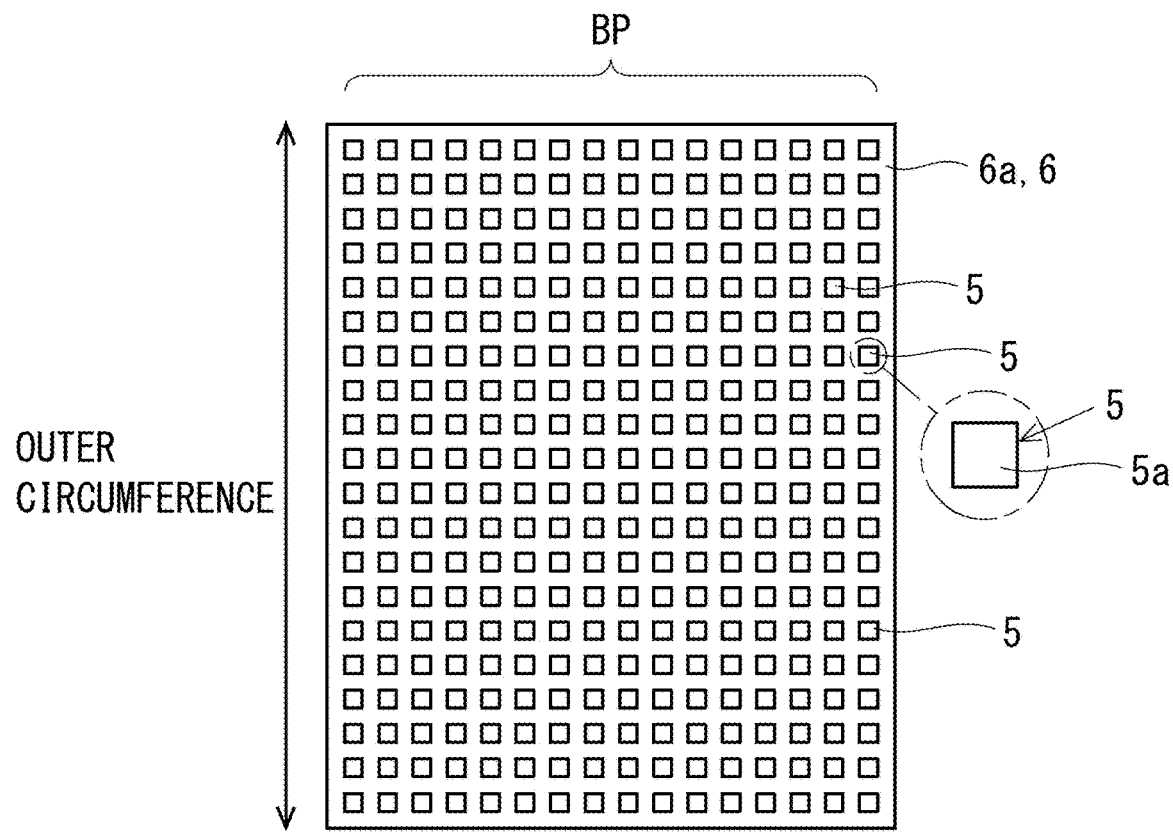
FIG. 4A is a conceptual view illustrating, in an exploded manner, the outer circumferential surface of a casing of the electronic cigarette according to Embodiment 1.
Figure 4B:
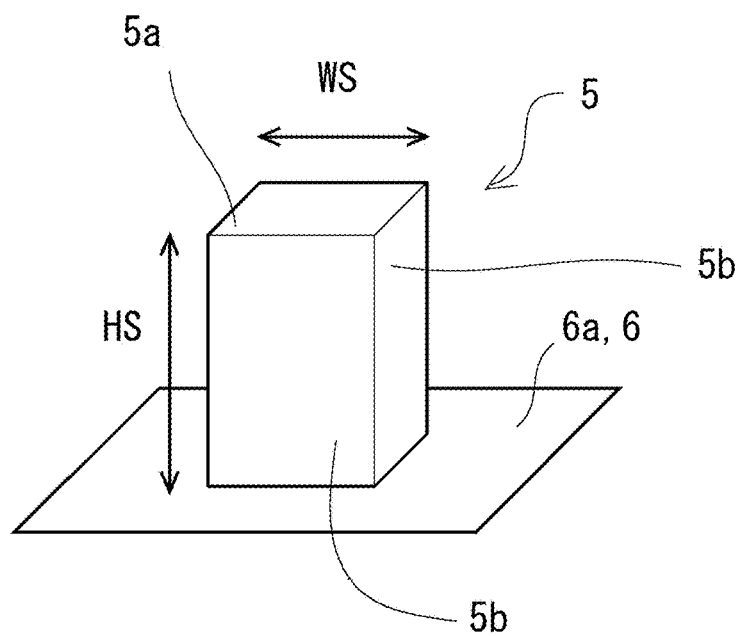
FIG. 4B is a perspective view of a protrusion provided in the casing of the electronic cigarette according to Embodiment 1.
Figure 5A:
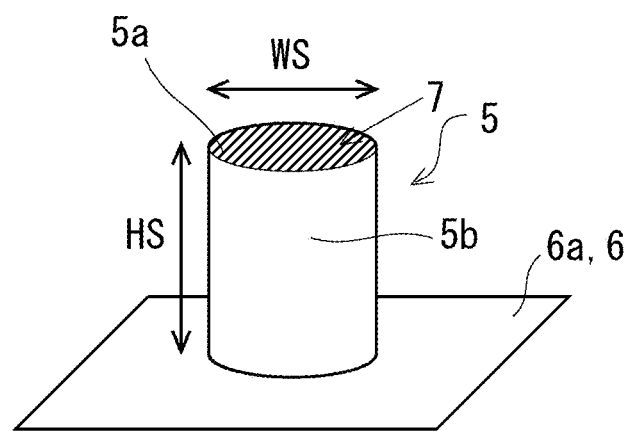
FIG. 5A is a view illustrating a variation of the shape of a protrusion constituting the bumpy pattern according to Embodiment 1.
Figure 5B:
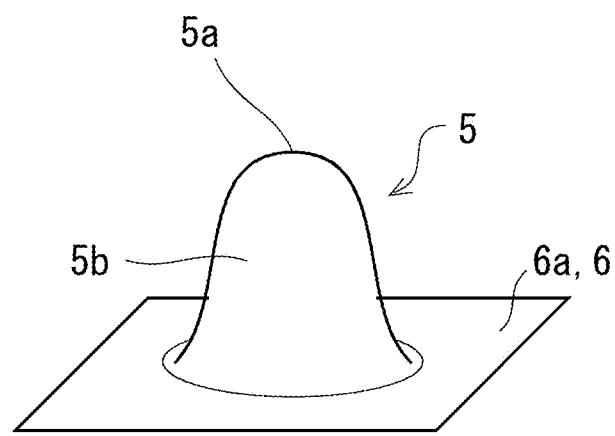
FIG. 5B is a view illustrating a variation of the shape of a protrusion constituting the bumpy pattern according to Embodiment 1.

Hereinafter, the heat dissipation structure of the electronic cigarette 1 will be described. As illustrated in FIGS. 1 to 3, on the outer circumferential surface of the casing CS of the electronic cigarette 1, a bumpy pattern BP made of metal which facilitates heat dissipation is provided. The bumpy pattern BP includes a plurality of protrusions 5 regularly aligned on the outer circumferential surface of the casing CS. FIG. 4A is a conceptual view illustrating, in an exploded manner, the outer circumferential surface of the casing CS of the electronic cigarette 1 according to Embodiment 1. FIG. 4B is a perspective view of the protrusion 5 provided on the casing CS of the electronic cigarette 1 according to Embodiment 1. In the present embodiment, each of the protrusions 5 constituting the bumpy pattern BP has a quadrangular prism shape as illustrated in FIG. 4B, but the protrusions 5 may have other shapes, such as variations illustrated as examples in FIGS. 5A and 5B. FIG. 5A illustrates an example of the protrusion 5 having a columnar shape. FIG. 5B illustrates an example of the protrusion 5 having a bell shape (bowl shape).

Reference numeral 6 illustrated in FIGS. 1 to 3 indicates an outer circumferential wall of the casing CS. The plurality of protrusions 5 constituting the bumpy pattern BP are formed in a protruding manner on an outer circumferential surface 6a of the outer circumferential wall 6 of the casing CS. As is apparent from FIGS. 1 to 3, the metal bumpy pattern BP is provided on the outer circumferential surface 6a of the casing CS at least at a position (range) where the electric heater 36 is placed. In short, in the electronic cigarette 1 according to the present embodiment, the metal bumpy pattern BP is arranged on the outer circumferential surface 6a of the casing CS to cover the side of the electric heater 36. Here, by providing the bumpy pattern BP on the outer circumferential surface 6a of the casing CS, it is possible to appropriately increase the surface area, that is, the heat dissipation area of the casing CS. Further, by making the bumpy pattern BP of a metal having excellent heat conductivity, it is possible to facilitate heat dissipation by the bumpy pattern BP.

As a result, heat is less likely to stay in the casing CS of the electronic cigarette 1, and it is possible to reduce the adverse effect on the respective components housed in the casing CS, for example, the electronic control unit 22 and the aerosol-generating liquid stored in the cartridge section 34. Furthermore, according to the present embodiment, since the bumpy pattern BP is formed by aligning the plurality of protrusions 5 on the outer circumferential surface 6a of the casing CS, it is possible not only to appropriately dissipate the heat inside the casing CS, but also to reduce the contact area between the fingers of the user holding the electronic cigarette 1 and the outer circumferential surface 6a of the casing CS. Consequently, the heat is less likely transferred to the fingers of the user holding the electronic cigarette 1, thereby producing the effect of less likely giving an unpleasant feeling to the user.

Here, in the longitudinal direction of the casing CS, a section where the bumpy pattern BP is formed is referred to as a "bumpy-pattern-arranged section Z1" (see FIG. 1). In the present embodiment, the electric heater 36 is arranged in the central portion, in the longitudinal direction, in the bumpy-pattern-arranged section Z1. Accordingly, it is possible to arrange the bumpy pattern BP in a well-balanced manner so that a position where the temperature is likely the highest is the center in the longitudinal direction of the electronic cigarette 1 (casing CS), thereby making it possible to efficiently dissipate the heat generated by the electric heater 36 to the outside (the atmosphere). Thus, it is possible to make it harder for the heat to stay in the casing CS of the electronic cigarette 1. The material that forms the bumpy pattern BP (protrusions 5) is not particularly limited as long as the material is made of metal, and may be, for example, stainless steel, aluminum, or the like.

Here, the rate of increase of the heat dissipation area (surface area) by providing the outer circumferential surface 6a of the casing CS with the bumpy pattern BP will be calculated. As an example of conditions, if the diameter of the electronic cigarette 1 (the outer diameter of the outer circumferential wall 6 of the casing CS) is 10 mm, the bumpy-pattern-arranged section Z1 is 30 mm, the shape of the protrusion 5 is a 1-mm cube and adjacent protrusions 5 are separated from each other by 1 mm, the rate of increase of the heat dissipation area (surface area) is about 202%. In the present embodiment, from the viewpoint of heat dissipation, the rate of increase of the surface area of the casing CS by providing the outer circumferential surface 6a of the casing CS with the bumpy pattern BP (protrusions 5) is preferably 20% or more.

Here, in the casing CS of the electronic cigarette 1, an end portion where the mouthpiece opening 31 is provided is referred to as a "mouthpiece-opening end 3a". In the electronic cigarette 1 according to the present embodiment, a no-bumpy-pattern-arranged section Z2 (see FIG. 1) in which the bumpy pattern BP is not provided is formed over a predetermined section from the mouthpiece-opening end 3a in the longitudinal direction of the casing CS. Thus, by not providing the bumpy pattern BP in a region on the mouthpiece-opening end 3a side of the casing CS, when the user holds in his or her mouth the mouthpiece opening 31 of the electronic cigarette 1, it is possible to prevent the mouth from touching the metal bumpy pattern BP arranged on the outer circumferential surface 6a of the bumpy-pattern-arranged section Z1 of the casing CS. The length of the no-bumpy-pattern-arranged section Z2 is not particularly limited, but is preferably 20 mm or more. That is, by not providing the bumpy pattern BP in the section of at least 20 mm from the mouthpiece-opening end 3a of the casing CS, it is possible to effectively prevent the lips of the user from touching the bumpy pattern BP when the electronic cigarette 1 is held in the mouth.

Moreover, in the electronic cigarette 1 of the present embodiment, as illustrated in FIGS. 4 and 5, a height dimension HS of the protrusion 5 of the bumpy pattern BP is preferably larger than a width dimension WS. Accordingly, when the height dimension HS is made relatively larger than the width dimension WS of the protrusion 5, the surface area (heat dissipation area) of the casing CS can be further increased by providing the outer circumferential surface 6a of the casing CS with the bumpy pattern BP. Consequently, it is possible to more easily dissipate the heat in the casing CS of the electronic cigarette 1 to the outside.

Further, as described above, by making the height dimension HS larger compared to the width dimension WS of the protrusion 5 of the bumpy pattern BP, the area of a side surface (side portion) 5b (see FIGS. 4 and 5) of the protrusion 5 (hereinafter referred to as the "side-portion area SS") can be relatively larger than the area of a top surface (top portion) 5a (see FIGS. 4 and 5) of the protrusion 5 (hereinafter referred to as the "top-portion area ST"). That is, it is possible to increase the ratio of the side-portion area SS to the entire surface area of the protrusion 5. Accordingly, when the user holds the electronic cigarette 1, the contact area between the fingers and the protrusions 5 can be smaller, thereby making it harder for the heat of the protrusions 5 from being transferred to the fingers of the user.

Furthermore, by increasing the ratio of the side-portion area SS to the entire surface area of the protrusion 5 as described above, it is possible to prioritize heat dissipation from the side surface 5b of the protrusion 5. Consequently, the temperature of the top surface 5a of the protrusion 5 is hard to be higher, and it is possible to make it harder to give an unpleasant feeling to the user who holds the electronic cigarette 1.

In addition, as illustrated in FIG. 5B, if each of the protrusions 5 of the bumpy pattern BP has a tapered shape toward the top surface (top portion) 5a, it is possible to further reduce the contact area between the fingers of the user and the protrusions 5 when the user holds the electronic cigarette 1. Therefore, it is possible to make it harder for the heat of the protrusions 5 to be transferred to the fingers of the user.

In the electronic cigarette 1 according to the present embodiment, a heat insulating material 7 is preferably provided on the top surface (top portion) 5a of each protrusion 5 constituting the bumpy pattern BP (see FIG. 5A). The heat insulating material 7 provided on the top surface 5a of each protrusion 5 constituting the bumpy pattern BP may be, for example, a heat insulating paint (heat insulating coating material) or the like. By applying a heat insulating paint or the like to the top surface 5a of the protrusion 5, the heat insulating properties of the top surface 5a of the protrusion 5 can be enhanced. Accordingly, it is possible to positively prevent the top surface 5a from heating up while prioritizing release of the heat generated by the electric heater 36 in the casing CS from the side surface 5b of the protrusion 5 to the outside. Therefore, the heat of the protrusions 5 is less likely transferred to the fingers of the user, and it is possible to appropriately prevent the heat from giving an unpleasant feeling to the user. The type of the heat insulating paint for coating the top surface 5a of the protrusion 5 is not particularly limited, but an example is a paint produced by making ceramics having high heat insulating properties into an emulsion (emulsifying and mixing of fine particles).

Figure 6:
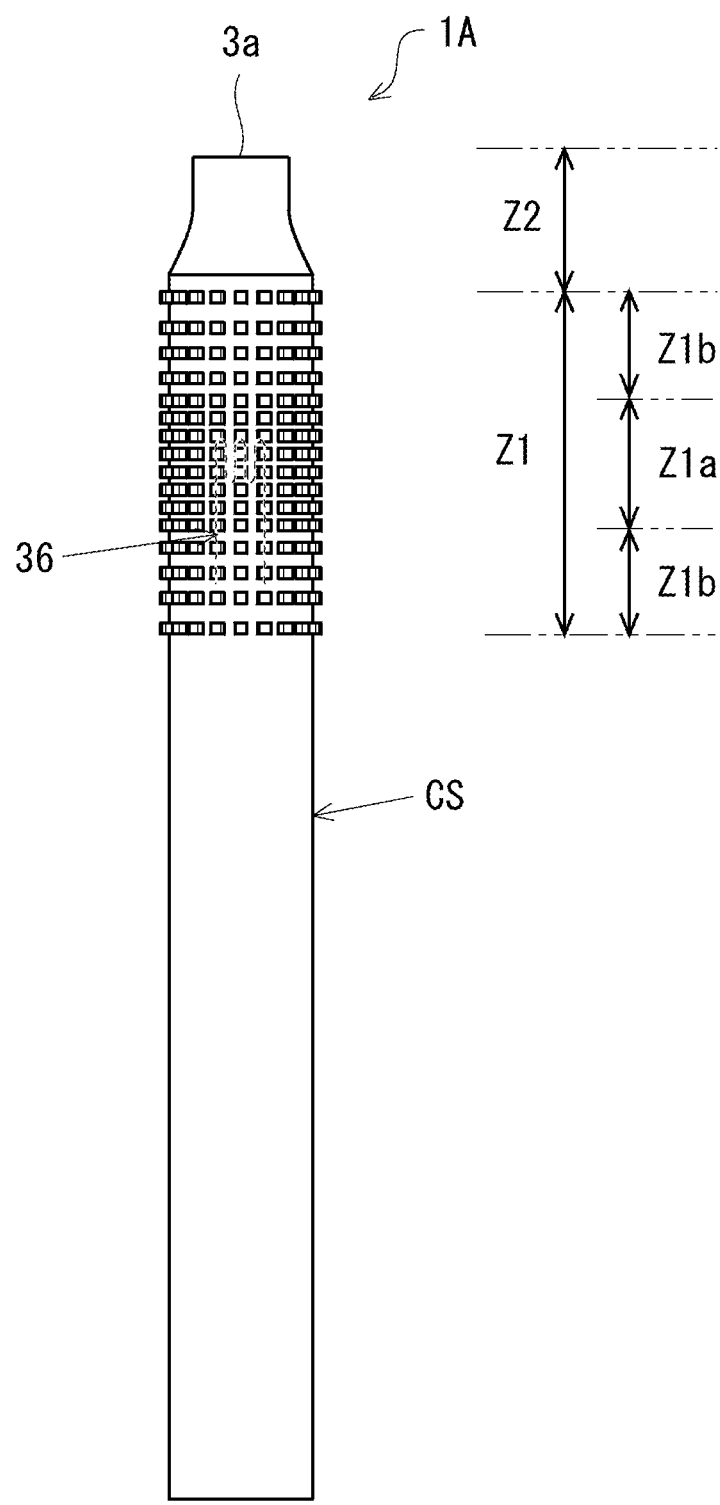
FIG. 6 is a view illustrating an electronic cigarette according to Modified Example 1 of Embodiment 1.

In the electronic cigarette 1 according to the present embodiment, the plurality of protrusions 5 are regularly aligned at constant intervals on the outer circumferential surface 6a of the casing CS, but the present invention is not limited by this. For example, the interval between the plurality of protrusions 5 aligned on the outer circumferential surface 6a of the casing CS may not be constant. FIG. 6 is a view illustrating an electronic cigarette 1A according to Modified Example 1 of Embodiment 1. The electronic cigarette 1A illustrated in FIG. 6 is the same as the aspect illustrated in FIGS. 1 to 3 in that the electric heating coil of the electric heater 36 is arranged in a central region Z1a of the bumpy-pattern-arranged section Z1, but the interval (pitch) between the protrusions 5 is changed in the central region Z1a of the bumpy-pattern-arranged section Z1 and end regions Z1b located on both sides of the central region Z1a.

In the example illustrated in FIG. 6, the interval between the protrusions 5 in the central region Z1a of the bumpy-pattern-arranged section Z1 is set smaller than the interval between the protrusions 5 in the end regions Z1b. Consequently, in the bumpy-pattern-arranged section Z1 of the casing CS, it is possible to arrange the protrusions 5 more densely in the central region Z1a than in the end regions Z1b. Accordingly, since the arrangement density of the protrusions 5 can be the highest in the central region Z1a corresponding to the position of the electric heater 36 in the bumpy-pattern-arranged section Z1 of the casing CS, heat from the electric heater 36 can be more appropriately dissipated to the outside.

While the preferred embodiment of the present invention has been described above, it is apparent to those skilled in the art that various modifications, improvements, combinations and the like can be made for the heating-type flavor inhaler according to the present invention. For example, in the above-described electronic cigarette 1 of Embodiment 1, the aerosol-generating liquid is stored in a manner in which the aerosol-generating liquid is impregnated into the liquid supply member 38 made of cotton fiber or the like arranged in the cartridge section 34, but it is also possible to adopt a tank system in which the aerosol-generating liquid is stored in a so-called liquid tank, or it is possible to provide an atomizer that evaporates the aerosol-generating liquid and the liquid tank as separate units. In the above-described embodiment, the example in which the bumpy pattern BP is formed by providing the protrusions 5 in a protruded pattern on the outer circumferential surface 6a of the outer circumferential wall 6 of the casing CS of the electronic cigarette 1 is described, but the present invention is not limited by this. For example, the bumpy pattern BP may be formed by providing a pattern of dent portions on the outer circumferential surface 6a of the outer circumferential wall 6 of the casing CS by, for example, cutting and the like. In this case, for example, a plurality of dent portions may be provided at constant intervals on the outer circumferential surface 6a of the casing CS. At that time, the protrusions 5 are formed between the adjacent dent portions, and the bumpy pattern BP is formed by a combination of the dent portions and the protrusions 5.

Figure 7:
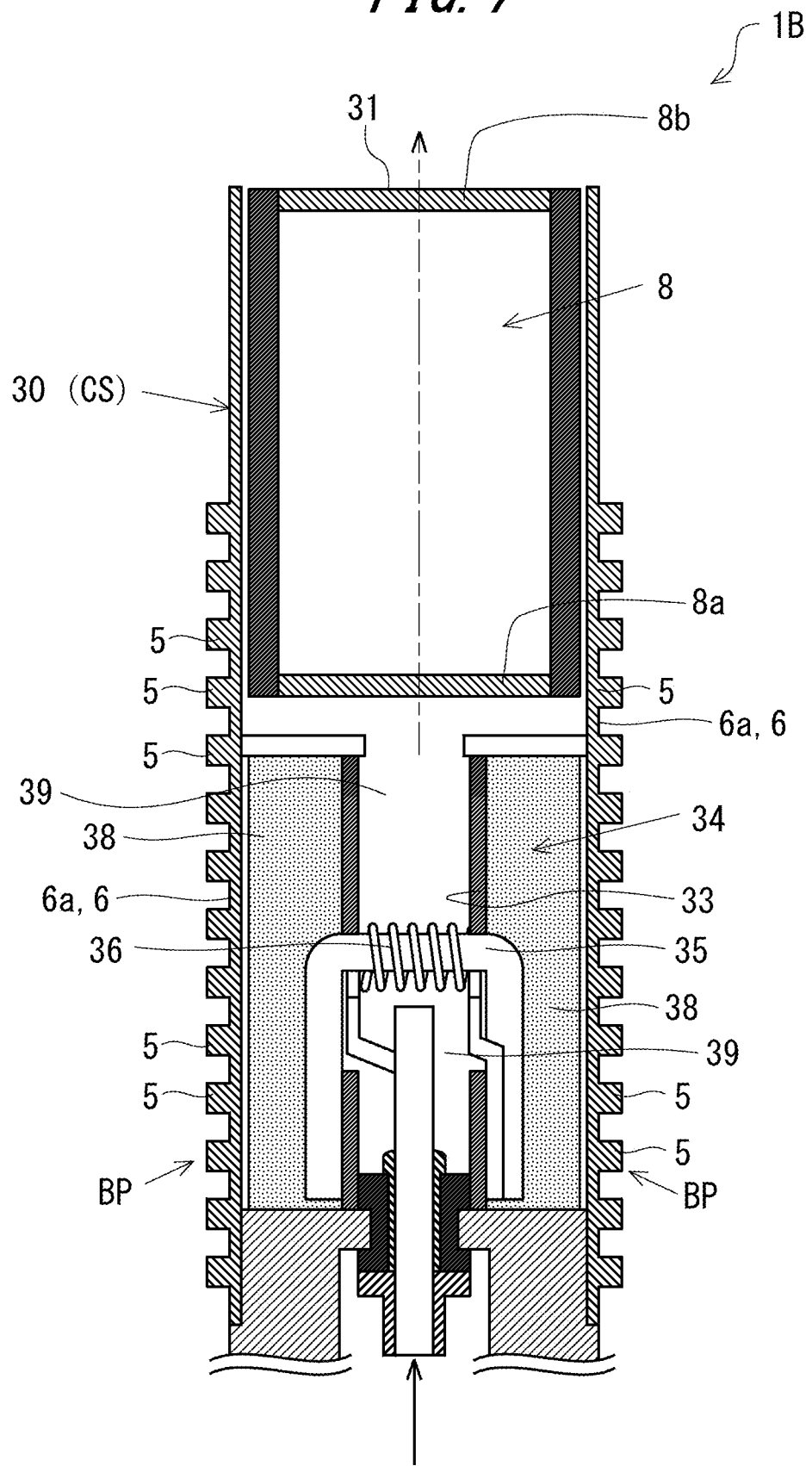
FIG. 7 is a view illustrating an electronic cigarette according to Modified Example 2 of Embodiment 1.

Further, for example, like an electronic cigarette 1B according to Modified Example 2 illustrated in FIG. 7, a tobacco cartridge 8 that contains tobacco leaves may be arranged at a rear stage of the cartridge section 34 of the cartomizer part 3. FIG. 7 partially illustrates only the cartomizer part 3 side of the electronic cigarette 1B. A front end face 8a and a rear end face 8b of the tobacco cartridge 8 are configured to allow passage of an aerosol generated in the cartomizer part 3. The aerosol generated in the cartomizer part 3 flows into the tobacco cartridge 8 from the front end face 8a. The user can inhale from the rear end face 8b the aerosol that has received a tobacco component and a flavoring component when the aerosol passes through the inside of the tobacco cartridge 8. In this type of electronic cigarette 1B, if the same heat dissipation structure as in Embodiment 1 is adopted, it is also possible to appropriately dissipate the heat generated by the electric heater 36 to the outside.

Figure 8:
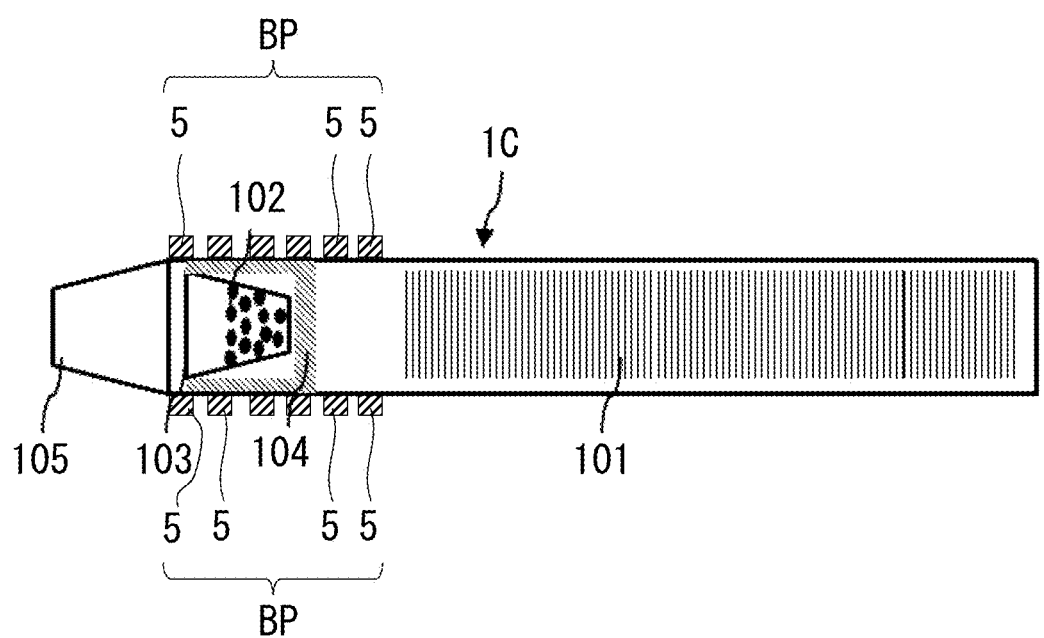
FIG. 8 is a view illustrating an electronic cigarette according to Modified Example 3 of Embodiment 1.

Moreover, the present invention is also applicable to an electronic cigarette as illustrated in FIG. 8. FIG. 8 is a view illustrating an electronic cigarette 1C according to Modified Example 3. FIG. 8 is a longitudinal sectional view when the cylindrical electronic cigarette 1C is cut in a longitudinal direction thereof. The electronic cigarette 1C has a battery 101, a pod 103 that contains a tobacco filler 102, an electric heater 104, and a mouthpiece 105. By filling the pod 103 with the tobacco filler 102 and heating the tobacco filler 102 in the pod 103 with the electric heater 104, an aerosol is generated and can be inhaled from the mouthpiece 105. In the example illustrated in FIG. 8, the bumpy pattern BP including a plurality of protrusions 5 made of metal is also provided on the outer circumferential surface 6a of a position of the casing CS at which the electric heater 104 is arranged. Thus, heat generated by the electric heater 104 can be appropriately dissipated to the outside.

REFERENCE SIGNS LIST

1 Electronic Cigarette (Heating-Type Flavor Inhaler)
2 Main body part
3 Cartomizer part
5 Protrusion
20 First casing
21 Battery
22 Electronic control unit
23 Suction detection sensor
24 LED
30 Second casing
31 Mouthpiece opening
32 second engagement part
34 Cartridge section
35 Wick
36 Electric heater
38 Liquid supply member
39 Internal passage
CS Casing
BP Bumpy pattern

The invention claimed is:
1. A heating-type flavor inhaler, comprising:
a casing having a mouthpiece opening and being cylindrical in overall shape;
a flavor generating source provided in the casing; and
a heater, provided in the casing, for electrically heating the flavor generating source,
wherein a bumpy pattern that is made of metal and facilitates heat dissipation is provided on an outer circumferential surface of at least a position of the casing at which the heater is arranged,
wherein the bumpy pattern comprises a plurality of protrusions,
wherein a heat insulating material is provided only on a top portion of each of the plurality of protrusions in the bumpy pattern, and
wherein the heat insulating material is ceramic.
2. The heating-type flavor inhaler according to claim 1, wherein the heater is arranged in a central region in a longitudinal direction of the casing, in a bumpy-pattern-arranged section where the bumpy pattern is formed.
3. The heating-type flavor inhaler according to claim 1, wherein the plurality of protrusions aligned on the outer circumferential surface of the casing.
4. The heating-type flavor inhaler according to claim 1, wherein a no-bumpy-pattern-arranged section where the bumpy pattern is not provided is formed over a predetermined section from a mouthpiece-opening end of the casing in a longitudinal direction.
5. The heating-type flavor inhaler according to claim 1, wherein a height dimension of each of the protrusions in the bumpy pattern is larger than a width dimension of the protrusion.
6. The heating-type flavor inhaler according to claim 1, wherein each of the protrusions in the bumpy pattern has a tapered shape toward a top portion.
7. A heating-type flavor inhaler, comprising:
a casing having a mouthpiece opening;
a flavor generating source provided in the casing; and
a heater, provided in the casing, for electrically heating the flavor generating source,
wherein a bumpy pattern that is made of metal and facilitates heat dissipation is provided on an outer circumferential surface of at least a position of the casing at which the heater is arranged, wherein the bumpy pattern comprises a plurality of protrusions wherein each of the plurality of protrusions has a total surface area, wherein each of the plurality of protrusions has a surface area covered by a heat insulating material, wherein the surface area covered by the heat insulating material is less than the total surface area, and wherein the heat insulating material is ceramic.

8. The heating-type flavor inhaler according to claim 7, wherein the plurality of protrusions are spaced in an axial direction and circumferential direction.

* * * * *